US012167926B2

(12) United States Patent
Nishii et al.

(10) Patent No.: US 12,167,926 B2
(45) Date of Patent: Dec. 17, 2024

(54) RADIOGRAPHIC SYSTEM, CONTROL APPARATUS, RADIOGRAPHIC METHOD, AND STORAGE MEDIUM

(71) Applicant: CANON KABUSHIKI KAISHA, Tokyo (JP)

(72) Inventors: Yuichi Nishii, Kanagawa (JP); Hikaru Tanaka, Kanagawa (JP); Yusuke Niibe, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 304 days.

(21) Appl. No.: 17/707,359

(22) Filed: Mar. 29, 2022

(65) Prior Publication Data

US 2022/0313199 A1    Oct. 6, 2022

(30) Foreign Application Priority Data

Mar. 31, 2021  (JP) ................................ 2021-059044
Mar. 31, 2021  (JP) ................................ 2021-059045
Mar. 31, 2021  (JP) ................................ 2021-059046

(51) Int. Cl.
*A61B 6/00* (2024.01)
*A61B 6/46* (2024.01)

(52) U.S. Cl.
CPC .............. *A61B 6/542* (2013.01); *A61B 6/465* (2013.01); *A61B 6/5205* (2013.01)

(58) Field of Classification Search
CPC ....... A61B 6/465; A61B 6/5205; A61B 6/542; A61B 6/4233; A61B 6/585; A61B 6/545; A61B 6/56; A61B 6/462; A61B 6/44; A61B 6/4208; A61B 6/40; A61B 6/563; A61B 6/566; A61B 6/54; A61B 6/52; A61B 6/4429; A61B 6/5241; A61B 6/025; A61B 6/06; A61B 6/08; A61B 6/4283; A61B 6/505; A61B 6/547; A61B 6/461; A61B 6/4266; A61B 6/42; A61B 6/00; H04N 5/32; H04N 7/18; H04N 21/44004; H04N 21/4223; H04N 21/23418; H04N 21/23406; H04N 7/183; H04N 21/44008; H04N 23/30; G06V 40/171; G06V 20/49;
(Continued)

(56) References Cited

U.S. PATENT DOCUMENTS

2013/0251106 A1 *  9/2013  Tajima ................. A61B 6/4233
                                                         378/97
2014/0177798 A1 *  6/2014  Kitagawa ................. A61B 6/56
                                                         378/62
(Continued)

FOREIGN PATENT DOCUMENTS

EP       4066742 A1 * 10/2022  ............. A61B 6/465
JP       4217505 B2      2/2009
JP    2021040903 A  *    3/2021

*Primary Examiner* — Irakli Kiknadze
(74) *Attorney, Agent, or Firm* — Canon U.S.A., Inc. IP Division

(57) ABSTRACT

A radiographic system that includes a radiation generation apparatus configured to emit radiation, a radiographic apparatus configured to generate a radiographic image based on the radiation, a control apparatus configured to communicate with the radiographic apparatus to receive the radiographic image and control operation, the radiographic system includes an obtaining unit configured to obtain a plurality of dose index values using the radiation image generated based on the radiation.

16 Claims, 14 Drawing Sheets

(58) Field of Classification Search
CPC . G06F 16/745; G01T 1/02; G01T 7/00; G01T 1/2018; G01T 1/20184; H05G 1/30; H05G 1/60; G03B 42/02; G06T 7/12; G06T 7/0012; G06T 7/13; G06T 2207/10116; G06T 2207/30101; G06T 2207/20021; G06T 2207/20081; G06T 2207/30061; G06T 2207/20084; G06T 2207/30048; G16H 30/40; G16H 50/20; G16H 50/30
USPC .................................................. 378/62, 97
See application file for complete search history.

(56) References Cited

U.S. PATENT DOCUMENTS

| | | |
|---|---|---|
| 2014/0205066 A1 | 7/2014 | Kitagawa |
| 2015/0182182 A1* | 7/2015 | Tajima .................. A61B 6/542 |
| | | 378/189 |
| 2016/0183908 A1* | 6/2016 | Hayashida ........... A61B 6/4291 |
| | | 378/207 |
| 2017/0172535 A1* | 6/2017 | Kim ...................... A61B 6/502 |

\* cited by examiner

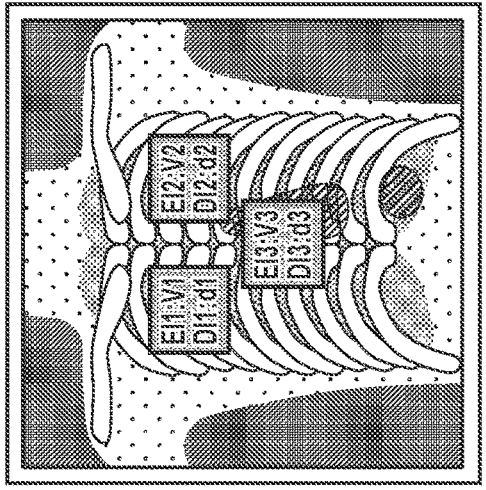
FIG. 8B
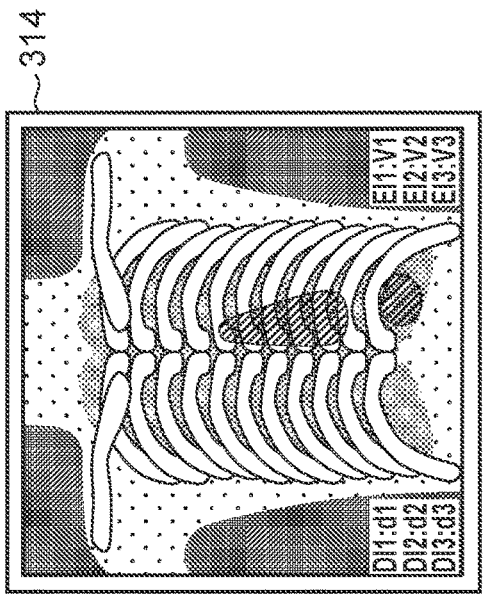
FIG. 8A
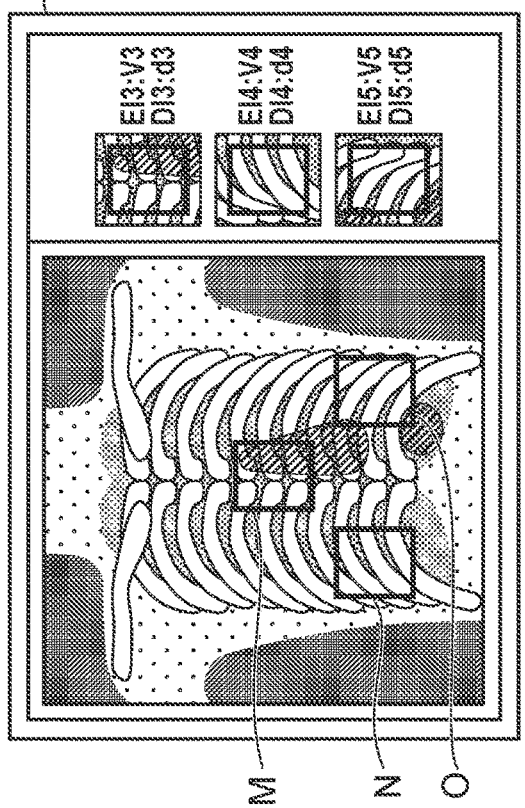
FIG. 8C
FIG. 8D
| IMAGE REGION | EI VALUE | EIt | DI |
|---|---|---|---|
| 1 | V1 | T1 | d1 |
| 2 | V2 | T2 | d2 |
| 3 | V3 | T3 | d3 |
| 4 | V4 | T4 | d4 |
| 5 | V5 | T5 | d5 |

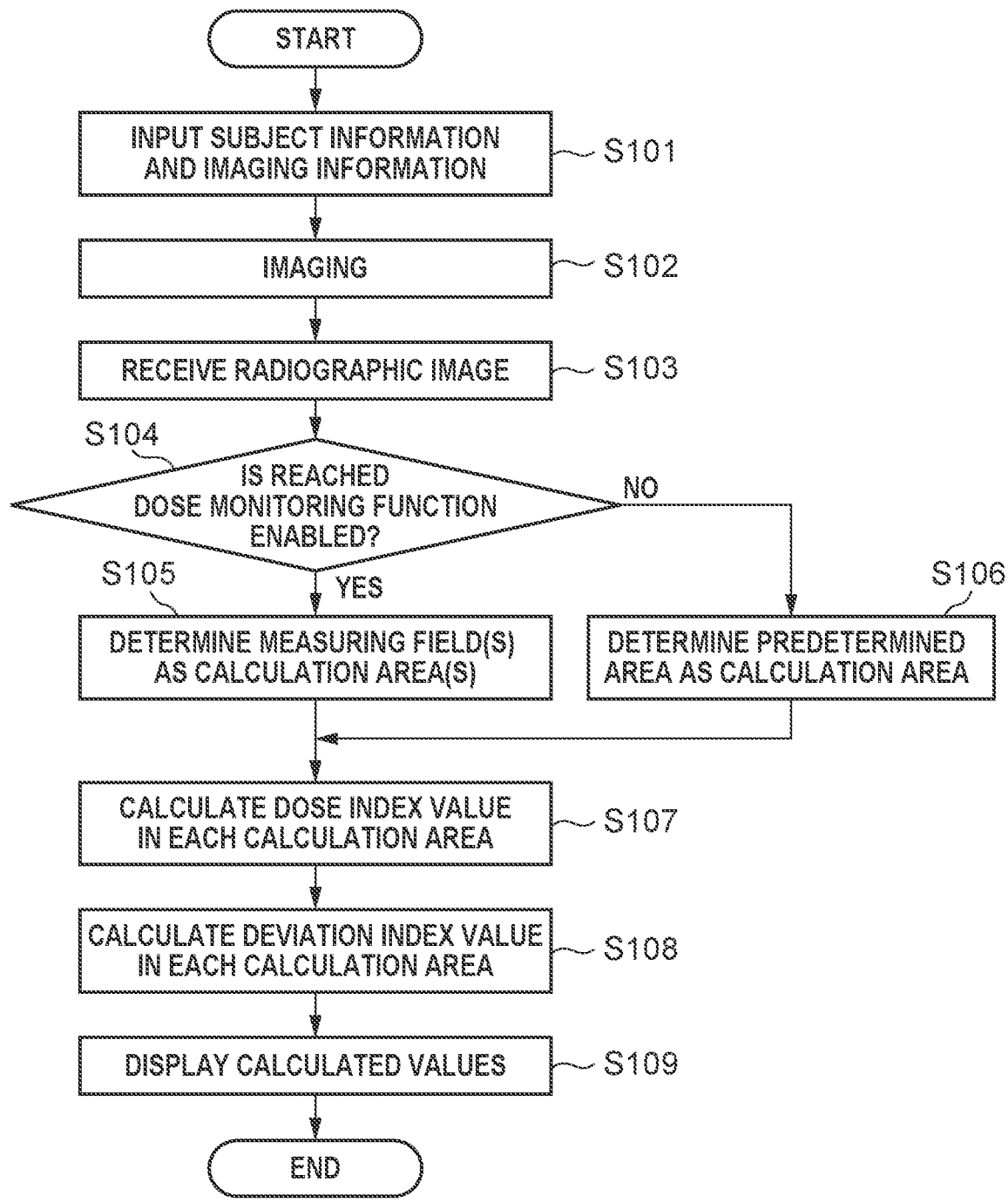

FIG. 11A
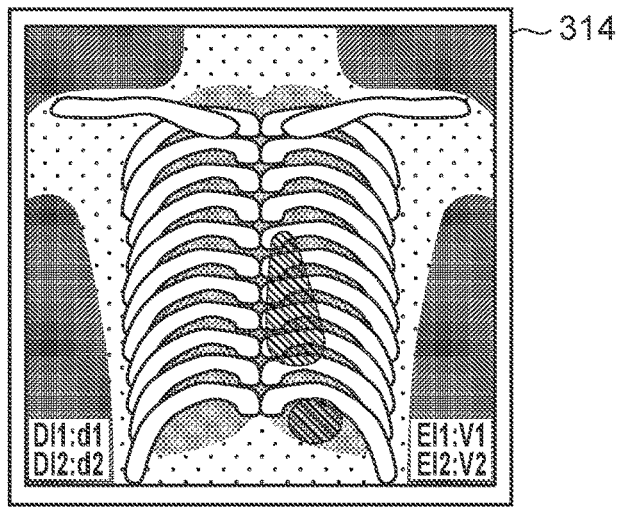
FIG. 11B
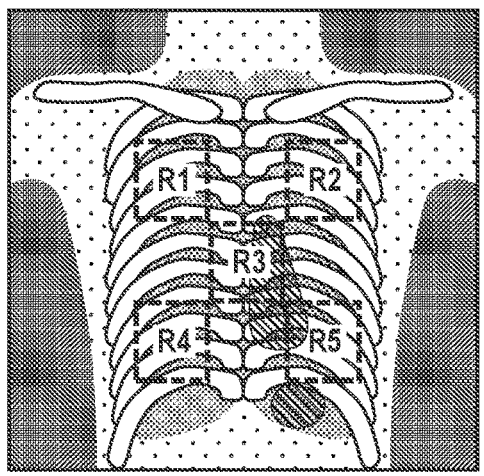
FIG. 11C
| IMAGE REGION | REACHED DOSE MONITORING FUNCTION | EI VALUE | EIt | DI |
|---|---|---|---|---|
| R1 | ON | V1 | T1 | d1 |
| R2 | ON | V2 | T2 | d2 |
| R3 | OFF | V3 | T3 | d3 |
| R4 | OFF | V4 | T4 | d4 |
| R5 | OFF | V5 | T5 | d5 |

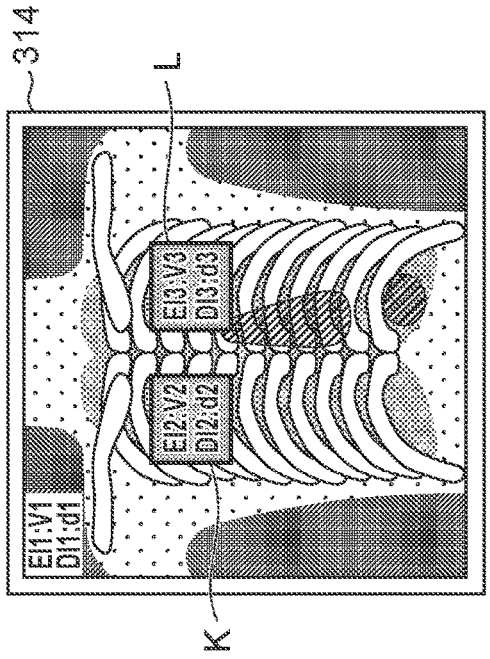
FIG. 12A
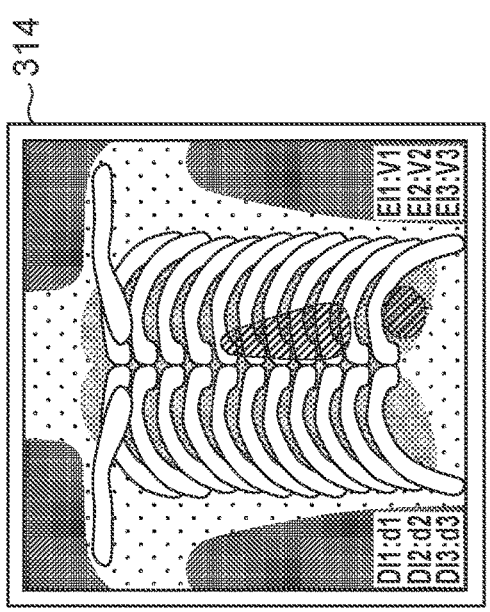
FIG. 12B
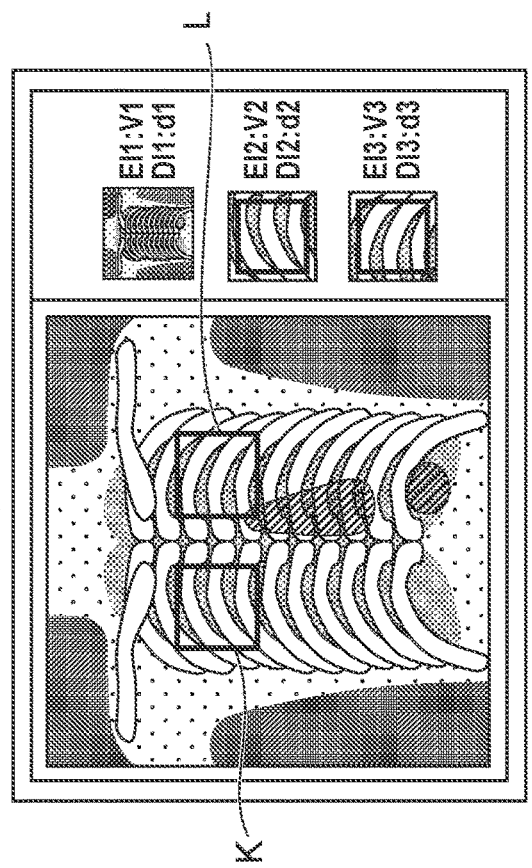
FIG. 12C
FIG. 12D
| IMAGE REGION | EI VALUE | EIt | DI |
|---|---|---|---|
| 1 | V1 | T1 | d1 |
| 2 | V2 | T2 | d2 |
| 3 | V3 | T3 | d3 |

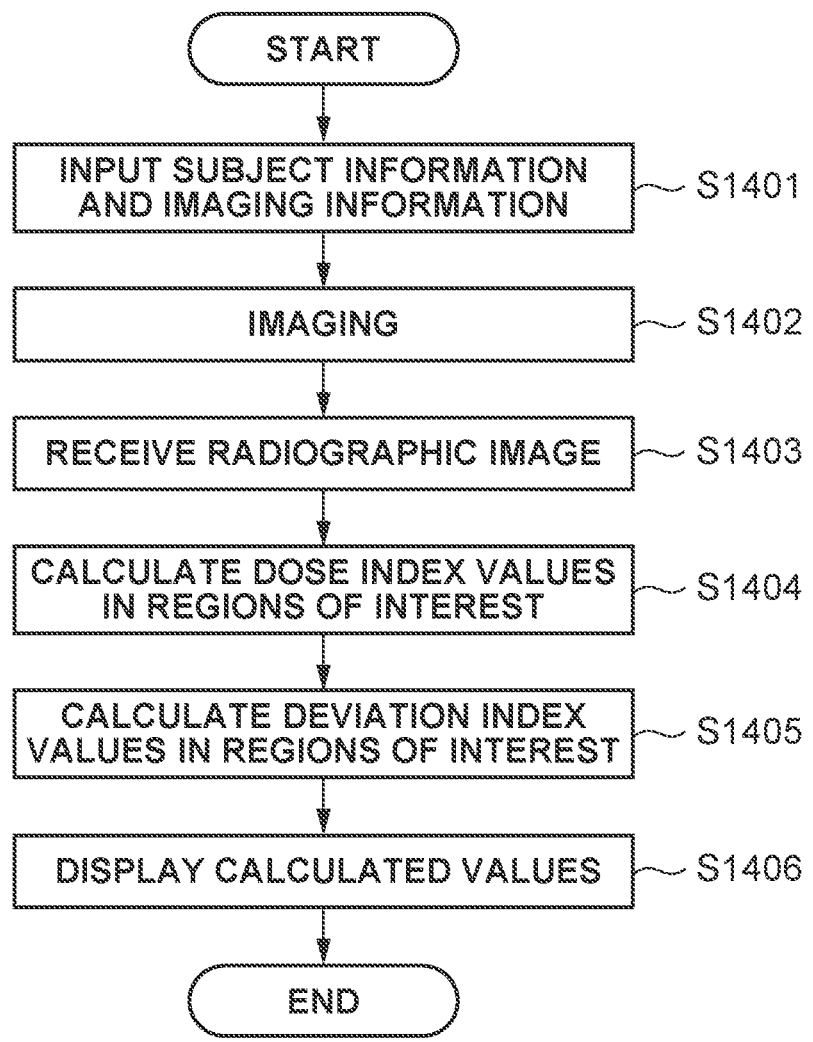

RADIOGRAPHIC SYSTEM, CONTROL APPARATUS, RADIOGRAPHIC METHOD, AND STORAGE MEDIUM

BACKGROUND OF THE INVENTION

Field of the Invention

The present invention relates to a radiographic system, a control apparatus, a radiographic method, and a storage medium.

Description of the Related Art

As radiographic apparatuses for use in medical image diagnosis and non-destructive inspection using radiation, such as X-rays, radiographic apparatuses that include a matrix substrate including a pixel array formed by combining switches, like thin-film transistors (TFTs), with conversion elements, like photoelectric conversion elements, have been put to practical use.

Several studies have been conducted to make radiographic apparatuses multifunctional. One of the approaches is to implement a built-in function for monitoring radiation irradiation. Such a function enables, for example, detection of a timing of starting radiation irradiation from a radiation source, detection of a timing of stopping the radiation irradiation, and detection of a radiation dosage or a cumulative dosage.

Japanese Patent No. 4217505 discusses a radiographic system including a radiographic apparatus, a radiation source, and an image control apparatus. The radiographic apparatus includes pixels for monitoring radiation irradiation. In a case where the radiographic system detects a timing of stopping irradiation, the radiographic apparatus transmits an irradiation stop signal to a radiation generation apparatus. While Japanese Patent No. 4217505 does not discuss specific control signals, the conventional radiation exposure control is performed by inputting an analog signal from a radiation receiving portion of an ion chamber or a photo timer into an exposure control unit inside the radiation generation apparatus. In response to detection of an integrated value of the analog signal and the like exceeding a predetermined threshold, the radiations are stopped, whereby automatic exposure control (AEC) is performed for dose control.

There is a technique for calculating a dose index value by analyzing a captured radiographic image, to display the dose index value on a graphical user interface (GUI). The dose index value is a numerical representation of the radiation dose received by the radiographic image detection apparatus.

An example of a dose index is an exposure index (EI). The dose index is a value for evaluating a dose used in radiographic imaging. EI is an index standardized by the International Electric Conference (IEC) as IEC 62494-1. Specifically, an area to calculate an EI value in a radiographic image is determined, and a representative value is extracted from among pixel values of pixels in the calculation area. A predetermined conversion is then performed on the extracted representative value, and the resulting dose index value is displayed. In each medical facility, EI information is managed and an EI value determined to be an optimum dose for radiographic images (for example, a minimum dose with satisfactory image quality) is set as a target value (Target Exposure Index) EIt. Determination of whether a dose is excessive or insufficient is then performed using a deviation (Deviation Index) DI between a calculated EI value and EIt to facilitate optimum imaging.

SUMMARY OF THE INVENTION

According to an aspect of the present invention, a radiographic system that includes a radiation generation apparatus configured to emit radiation, a radiographic apparatus configured to generate a radiographic image based on the radiation, a control apparatus configured to communicate with the radiographic apparatus to receive the radiographic image and control operation, the radiographic system includes an obtaining unit configured to obtain a plurality of dose index values using the radiation image generated based on the radiation.

Further features of the present invention will become apparent from the following description of exemplary embodiments with reference to the attached drawings.

BRIEF DESCRIPTION OF THE DRAWINGS

FIGS. 8A to 8D are diagrams each illustrating a display example of dose index values.

FIG. 10 is a flowchart illustrating an operation example of the radiographic system.

FIGS. 11A to 11C are diagrams each illustrating a display example of dose index values.

FIGS. 12A to 12D are diagrams each illustrating a display example of dose index values.

FIG. 14 is a flowchart illustrating an operation example of a radiographic system.

DESCRIPTION OF THE EMBODIMENTS

For example, in a case where automatic exposure control (AEC) is used when lung fields are imaged, radiographic imaging is typically performed on measuring fields set at both lungs. In such a case, by stopping radiation irradiation at a timing of when an irradiation dose for both lungs reaches an optimum dose, an irradiation dose in the radiation irradiation can be reduced. Consequently, it is desirable that an exposure index (EI) value and a target value EIt are displayed or set based on the measuring fields.

However, since conventional apparatuses display the EI value and set the target value EIt as a dose index of the entire radiographic image, whether a sufficient amount of radiation is incident on the AEC measuring fields is unable to be determined based on the numerical values.

Exemplary embodiments of the present invention have been achieved in view of the foregoing issue, and are directed to providing a radiographic system where an operator can appropriately determine whether a desirable amount of radiation is incident on measuring fields during radiographic imaging using AEC.

The present exemplary embodiments can also be directed to providing operations and effects that are derived from configurations described below and not obtainable by the conventional art.

Figure 1:
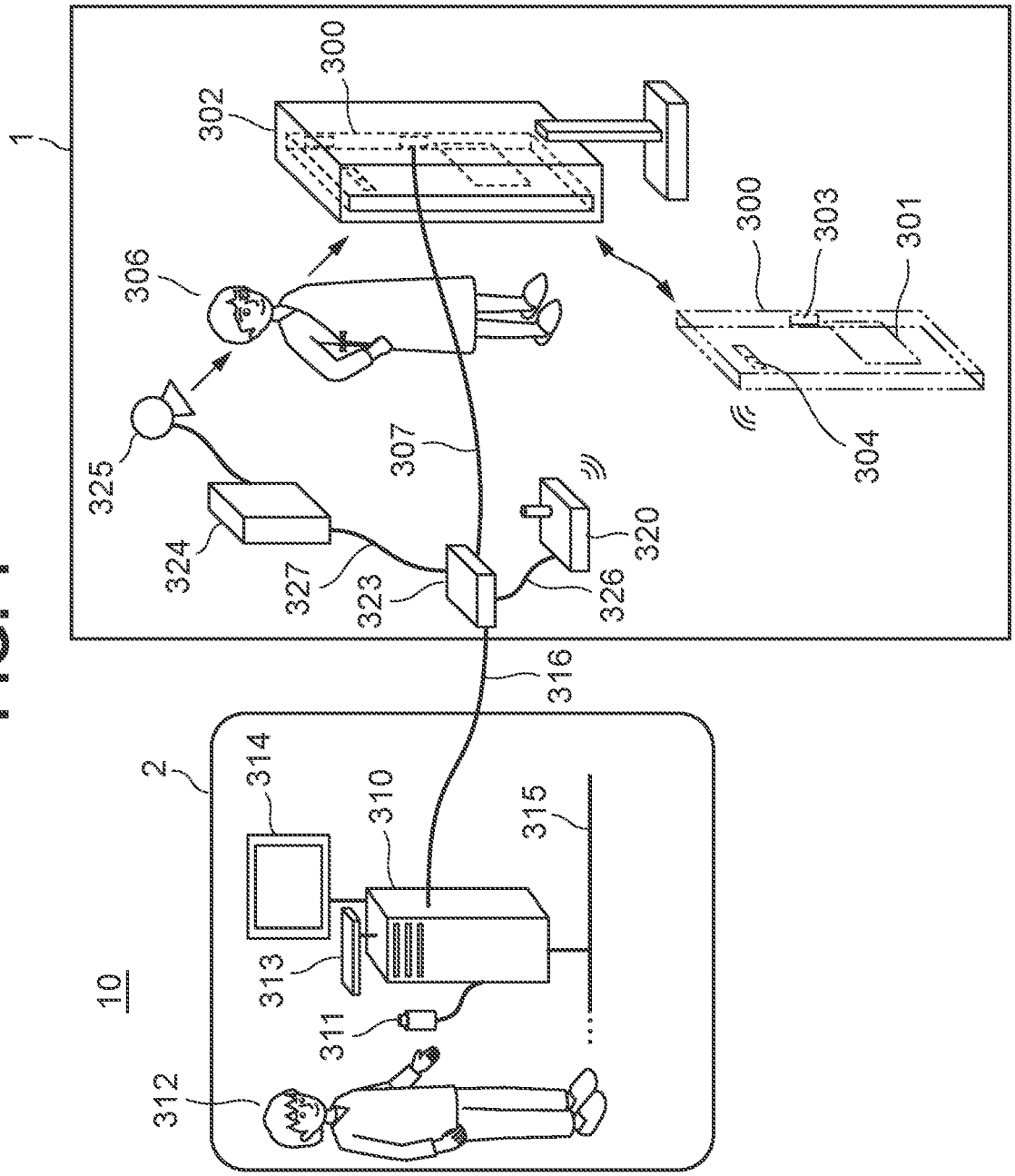
FIG. 1 is a diagram illustrating an example of a radiographic system.

A radiographic system according to a first exemplary embodiment will be described below with reference to the drawings. FIG. 1 is a diagram illustrating a radiographic system according to the present exemplary embodiment.

As illustrated in FIG. 1, a radiographic system 10 is disposed in a radiation chamber 1 where radiographic imaging using radiation irradiation is performed and a control chamber 2 in the vicinity of the radiation chamber 1.

The radiation chamber 1 includes, as the radiographic system 10, a radiographic apparatus 300, an upright stand 302, a first communication cable 307, an access point (AP) 320, a communication control apparatus 323, a radiation generation apparatus 324, a radiation source 325, a second communication cable 326, and a third communication cable 327.

The control chamber 2 includes, as the radiographic system 10, a control apparatus 310, an irradiation switch 311, an input apparatus 313, a display apparatus 314, an in-hospital local area network (LAN) 315, and a fourth communication cable 316.

The configuration of the apparatuses installed in the radiation chamber 1 and the control chamber 2 is not limited to the foregoing. Any configuration that functions as the radiographic system 10 may be employed.

The radiographic apparatus 300 includes a power supply control unit 301 including a battery, a wired communication unit 303, and a wireless communication unit 304. The radiographic apparatus 300 detects radiation transmitted through a subject 306 and generates a radiographic image. An image according to the present exemplary embodiment refers not only to an image being displayed on a display unit but also to an image being stored in a database or storage unit as image data.

The wired communication unit 303 performs information exchange by cable connection using a communication standard of predetermined agreement or a standard, such as the Ethernet (registered trademark), for example.

The wireless communication unit 304 includes a circuit substrate equipped with an antenna and a communication integrated circuit (IC), for example. The circuit substrate equipped with the communication IC performs communication processing using a wireless LAN-based protocol via the antenna. The frequency band, standard, and method of the wireless communication are not limited in particular. A proximity wireless communication method, such as near field communication (NFC) and Bluetooth®, or a method such as ultra-wideband (UWB) may be used. The wireless communication unit 304 may support a plurality of wireless communication methods and perform communication by selecting one from among the supported wireless communication methods as appropriate.

The upright stand 302 is a pedestal to which the radiographic apparatus 300 can be attached, to perform radiographic imaging in an upright position. The radiographic apparatus 300 can be detachably attached to the upright stand 302, and can capture images both in an attached state and a detached state.

The first communication cable 307 is a cable for connecting the radiographic apparatus 300 and the communication control apparatus 323.

The AP 320 performs wireless communication with the radiographic apparatus 300. For example, the AP 320 is used to relay communication between the radiographic apparatus 300 and the control apparatus 310 and between the radiographic apparatus 300 and the radiation generation apparatus 324 in using the radiographic apparatus 300 detached from the upright stand 302.

While FIG. 1 illustrates a case where the communication is performed via the AP 320, either the radiographic apparatus 300 or the communication control apparatus 323 may serve as an AP to perform direct communication without the intermediary of the AP 320.

The communication control apparatus 323 controls communication between the AP 320, the radiation generation apparatus 324, and the control apparatus 310.

The radiation generation apparatus 324 controls the radiation source 325 to emit radiation based on a predetermined irradiation condition.

The radiation source 325 irradiates the subject 306 with radiation based on control by the radiation generation apparatus 324.

The second communication cable 326 is a cable for connecting the AP 320 and the communication control apparatus 323.

The third communication cable 327 is a cable for connecting the radiation generation apparatus 324 and the communication control apparatus 323.

The control apparatus 310 communicates with the radiation generation apparatus 324 and the radiographic apparatus 300 via the communication control apparatus 323, and controls the radiographic system 10 in a centralized manner.

The irradiation switch 311 inputs a radiation irradiation timing based on an operation by an operator 312.

The input apparatus 313 is an apparatus for inputting instructions from the operator 312. Various input devices, such as a keyboard and a touch panel, are used as the input apparatus 313.

The display apparatus 314 is an apparatus for displaying an image-processed radiographic image and a graphical user interface (GUI). An example of the display apparatus 314 is a display.

The in-hospital LAN 315 is a backbone network in the hospital.

The fourth communication cable 316 is a cable for connecting the control apparatus 310 and the communication control apparatus 323 in the radiation chamber 1.

Figure 2:
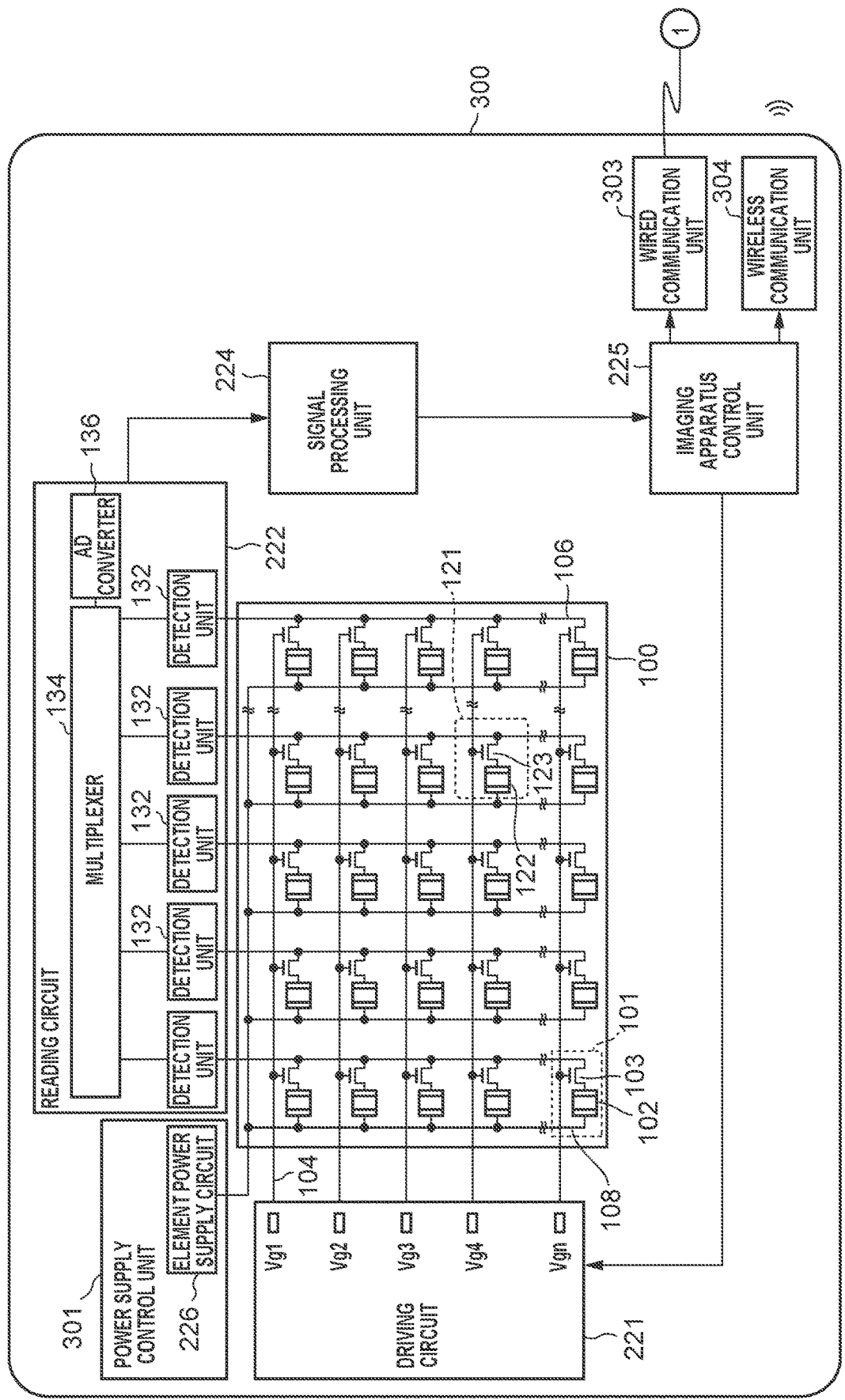
FIG. 2 is a diagram illustrating an example of a radiographic apparatus.

FIG. 2 is a diagram illustrating the radiographic apparatus 300. As illustrated in FIG. 2, the radiographic apparatus 300 includes a radiation detector 100. The radiation detector 100 has a function of detecting irradiating radiation. The radiation detector 100 includes a plurality of pixels arranged to form a plurality of rows and a plurality of columns. In the following description, an area of the radiation detector 100 where the plurality of pixels is arranged will be referred to as a radiation detection area. The plurality of pixels includes imaging pixels 101 for obtaining a radiographic image or irradiation information, and correction pixels 121 for removing dark current components and crosstalk components.

In the present exemplary embodiment, the use of the imaging pixels 101 for obtaining irradiation information will be described. The imaging pixels 101 will therefore be hereinafter referred to as detection pixels 101. The detection pixels 101 may be used for a purpose of obtaining radiographic images or for a purpose of obtaining irradiation information. Alternatively, the detection pixels 101 may obtain both radiographic images and irradiation information. In other words, the detection pixels 101 may be configured to obtain at least either radiographic images or irradiation information.

The detection pixels 101 each include a first conversion element 102 for converting radiation into an electrical signal, and a first switch 103 disposed between a column signal line 106 and the first conversion element 102.

The first conversion element 102 includes a scintillator, which is for converting radiation into light, and a photoelectric conversion element, which is for converting the light into an electrical signal. The scintillator is typically formed in a sheet shape to cover the radiation detection area, and shared by the plurality of pixels. Alternatively, the first conversion element 102 includes a conversion element that directly converts radiation into light.

The first switch 103 includes a thin-film transistor (TFT) having an active region formed of a semiconductor, such as amorphous silicon and polycrystalline silicon (desirably polycrystalline silicon), for example.

The correction pixels 121 each include a second conversion element 122 for converting radiation into an electrical signal, and a second switch 123 disposed between a column signal line 106 and the second conversion element 122.

Since the second conversion element 122 and the second switch 123 are similar to the first conversion element 102 and the first switch 103, respectively, the redundant descriptions will be omitted.

Figure 3:
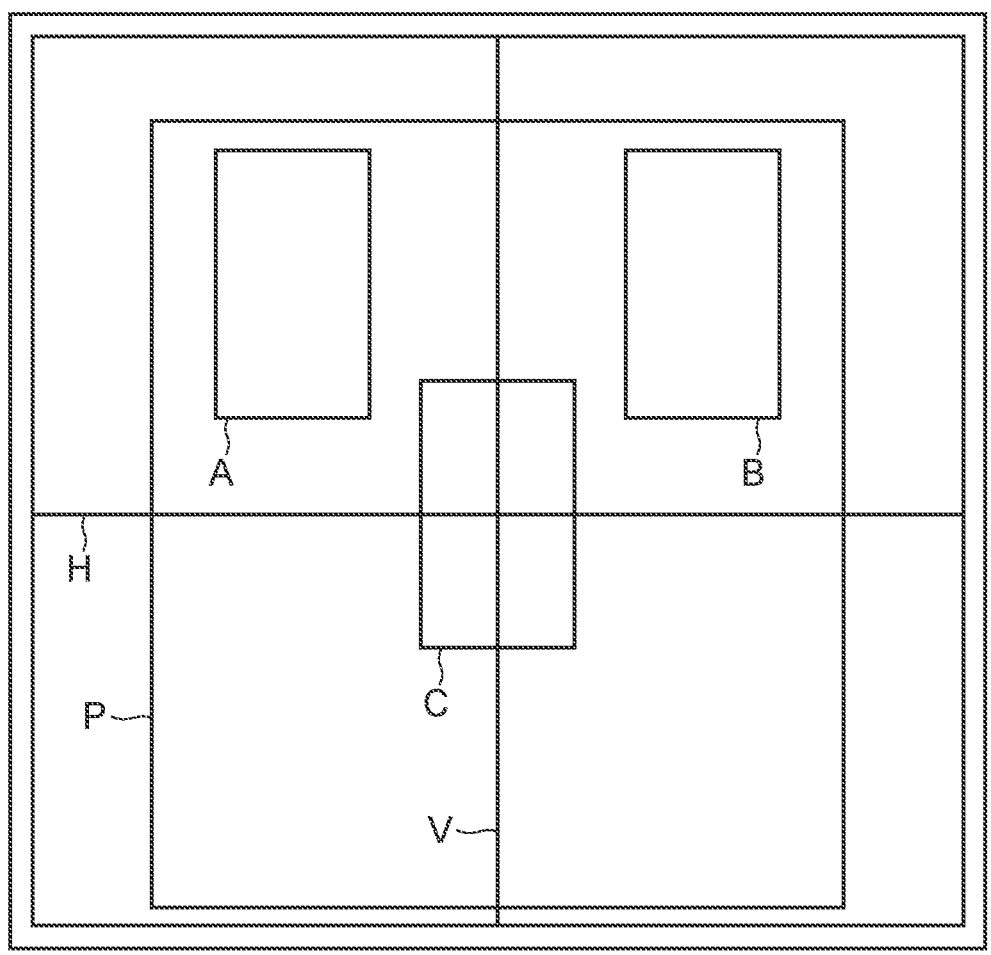
FIG. 3 is a diagram illustrating an example of a layout of measuring fields and an arbitrary area(s) (an entire area of a radiographic image, an area selected by an operator, an area corresponding to an imaging site, or the like).
Figure 4:
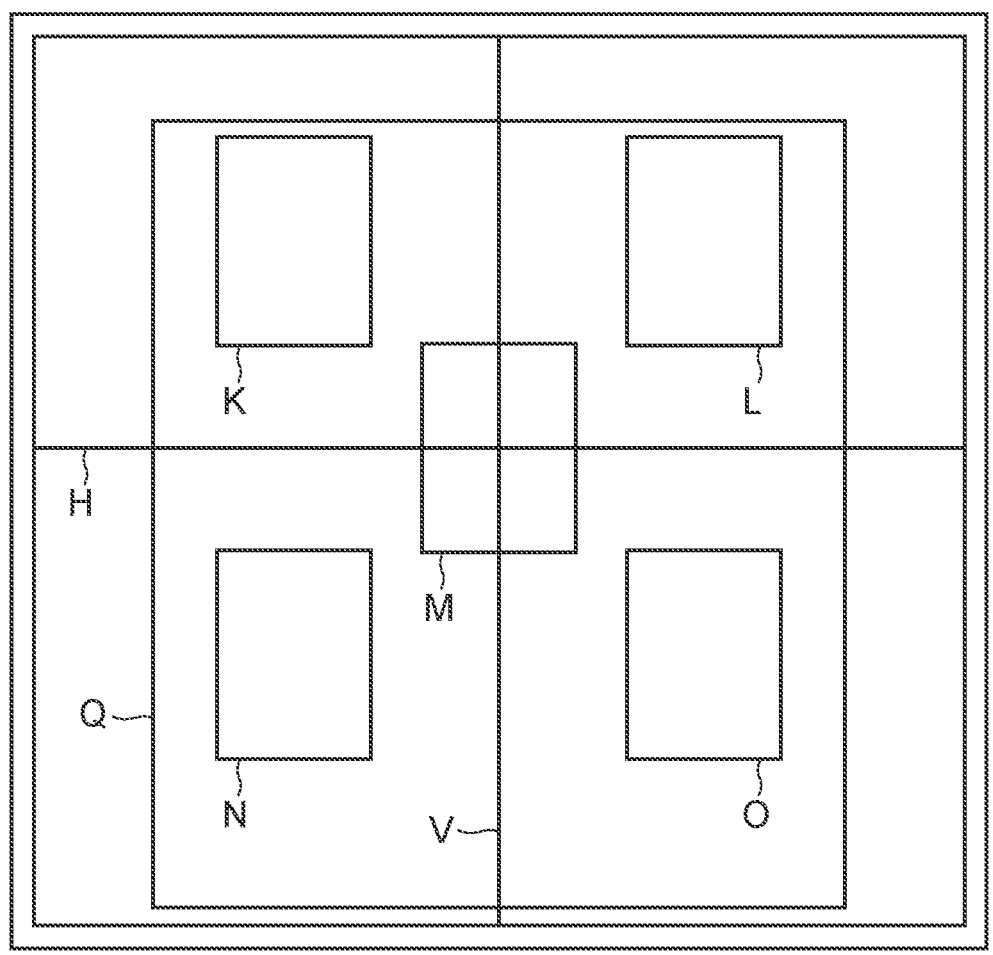
FIG. 4 is a diagram illustrating an example of a layout of measuring fields and an arbitrary area(s) (an entire area of a radiographic image, an area selected by an operator, an area corresponding to an imaging site, or the like).

An area where both detection pixels 101 and correction pixels 121 for obtaining irradiation information are arranged is laid out at any position within the radiation detection area of the radiographic apparatus 300. For example, similar to a conventional separate AEC sensor, such an area may be laid out at a plurality of positions like areas A to C in FIG. 3, or areas K to O in FIG. 4.

The radiographic apparatus 300 includes a plurality of column signal lines 106 and a plurality of drive lines 104.

Each of the column signal lines 106 corresponds to different one of the columns in the radiation detection area. Each of the drive lines 104 corresponds to different one of the rows in the radiation detection area.

The drive lines 104 are driven by a driving circuit 221.

A first electrode of the first conversion element 102 and a first electrode of the second conversion element 122 are connected to a first main electrode of the first switch 103 and a first main electrode of the second switch 123, respectively. A second electrode of the first conversion element 102 and a second electrode of the second conversion element 122 are each connected to a bias line 108. Each of the bias lines 108 extends in the column direction and is connected to the second electrodes of a plurality of the conversion elements 102 and 122 arranged in a column direction in common.

The bias lines 108 receive a bias voltage Vs from an element power supply circuit 226. The bias voltage Vs is supplied from the element power supply circuit 226.

The power supply control unit 301 includes the battery and a direct-current-to-direct-current (DCDC) converter. The power supply control unit 301 includes the element power supply circuit 226, and generates an analog circuit power supply voltage and a digital circuit power supply voltage. The digital circuit power supply voltage is for use in driving control and communication.

A second main electrode of the first switch 103 each in a plurality of the detection pixels 101 and a second main electrode of the second switch 123 each in a plurality of the correction pixels 121, in a single column, are connected to a column signal line 106. A control electrode of the first switch 103 each in the plurality of the detection pixels 101 and a control electrode of the second switch 123 each in the plurality of the correction pixels 121, in a single row, are connected to a drive line 104. The plurality of the column signal lines 106 is connected to a reading circuit 222. Here, the reading circuit 222 includes a plurality of detection units 132, a multiplexer 134, and an analog-to-digital (AD) converter 136.

The column signal lines 106 are each connected to corresponding one of the detection units 132 in the reading circuit 222. Here, one column signal line 106 corresponds to one detection unit 132.

The detection units 132 each include a differential amplifier, for example. The multiplexer 134 selects the detection units 132 in predetermined order and supplies a signal from the selected one of the detection units 132 to the AD converter 136.

The AD converter 136 converts the supplied signal into a digital signal and outputs the digital signal.

A signal processing unit 224 outputs information indicating irradiation of the radiographic apparatus 300 with radiation, based on the output of the reading circuit 222 (AD converter 136). Specifically, for example, the signal processing unit 224 performs characteristic correction processing, detects irradiation with radiation, and calculates a radiation dosage and a cumulative dosage. The characteristic correction processing includes removing dark current components and crosstalk components of the radiographic apparatus 300 by using the correction pixels 121.

An imaging apparatus control unit 225 controls, for example, the driving circuit 221 and the reading circuit 222, based on information from the signal processing unit 224 and control commands from the control apparatus 310.

Figure 5:
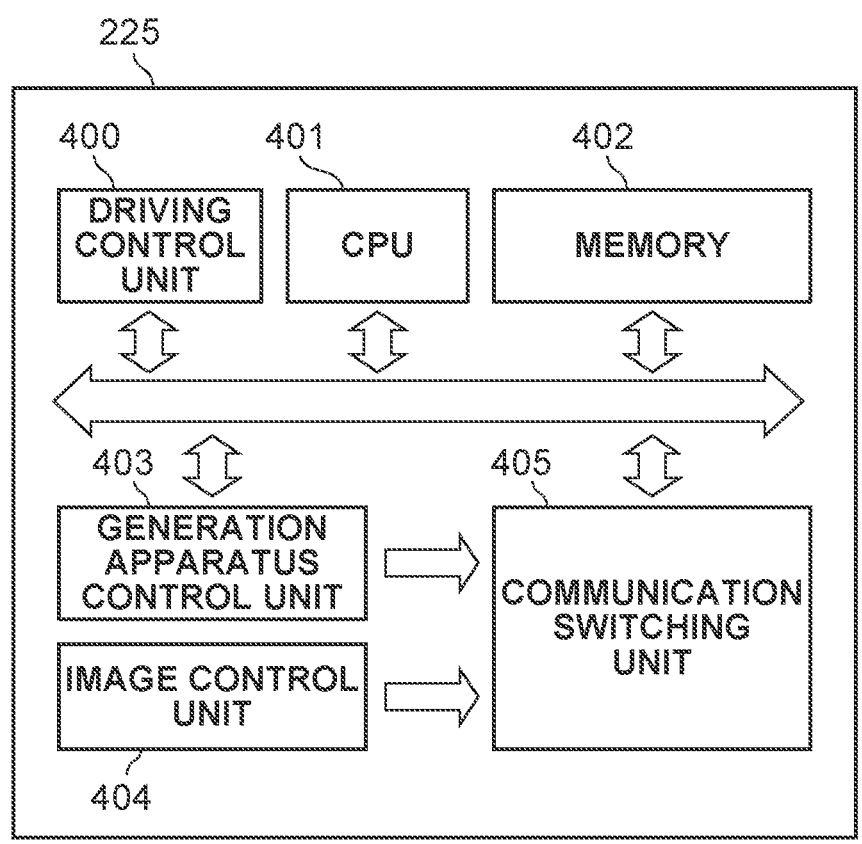
FIG. 5 is a diagram illustrating an example of an imaging apparatus control unit in the radiographic apparatus.

FIG. 5 is a diagram illustrating the imaging apparatus control unit 225 of the radiographic apparatus 300. As illustrated in FIG. 5, the imaging apparatus control unit 225 includes a driving control unit 400, a central processing unit (CPU) 401, a memory 402, a generation apparatus control unit 403, an image control unit 404, and a communication switching unit 405.

The driving control unit 400 controls the driving circuit 221 and the reading circuit 222, based on information from the signal processing unit 224 and control commands from the control apparatus 310. The driving control unit 400 communicates with the radiographic apparatus 300 to receive a radiographic image and to control operation.

The CPU 401 controls the entire radiographic apparatus 300 using programs and various types of data stored in the memory 402.

The memory 402 stores programs and various types of data that the CPU 401 uses in executing processing, for example. The various types of data include various types of data obtained by the processing of the CPU 401 and radiographic images.

The generation apparatus control unit 403 controls communication with the radiation generation apparatus 324, based on information from the signal processing unit 224 and information from the driving control unit 400.

The generation apparatus control unit 403 and the radiation generation apparatus 324 exchange information about control of the radiation generation apparatus 324 (such as notifications to start and stop radiation irradiation, a radiation dosage, and a cumulative dosage).

In a case where a radiation dosage in a radiation detection area (measuring field) as a monitoring target of a radiation dosage reaches a reference threshold (target cumulative dosage), the generation apparatus control unit 403 notifies the radiation generation apparatus 324 of a stop notification among pieces of information about the control of the radiation generation apparatus 324. Examples of the measuring field include the areas A to C in FIG. 3 and the areas K to O in FIG. 4. The detection pixels 101 included in the radiation detection area (measuring field) correspond to an example of a dose detection unit for detecting a dose reached to the dose detection unit during radiation irradiation. The generation apparatus control unit 403 detects radiation incident on the measuring field by using the detection pixels 101, and calculates a cumulative dosage that is a cumulative value of doses (reached doses) detected by the signal processing unit 224 during a predetermined period.

The generation apparatus control unit 403 issues a stop notification at a timing of when a radiation dosage in a measuring field selected as a monitoring target reaches the reference threshold (hereinafter, this procedure is referred to as a reached dose monitoring function). In a case where a plurality of measuring fields is selected as a monitoring target, the following three control methods can be employed, for example. In an OR control method, the generation apparatus control unit 403 issues a stop notification at a timing of when a cumulative value of any one of the selected measuring fields reaches the target cumulative dosage. In an average control method, the generation apparatus control unit 403 issues a stop notification at a timing of when an average of cumulative values of a plurality of selected measuring fields reaches a value set as the target cumulative dosage. In an AND control method, the generation apparatus control unit 403 issues a stop notification at a timing of when all cumulative values of a plurality of selected measuring fields reach a value set as the target cumulative dosage. Control methods other than the foregoing methods may be used. Two or more of the foregoing methods may be used in combination.

If, for example, four measuring fields R1, R2, R4, and R5 in FIGS. 11A to 11C are selected, it can be determined that irradiation of two juxtaposed measuring fields with as much radiation as the target cumulative dosage is sufficient since the radiographic apparatus 300 is used in more than one orientation. In such a case, the generation apparatus control unit 403 may specify a combination of operators like (R1 AND R2) OR (R2 AND R5) OR (R5 AND R4) OR (R4 AND R1), and issue a stop notification in response to two measuring fields reaching the target cumulative dosage first. While, the OR, average, and control methods are described as examples, other control methods and operators (such as NAND, NOR, and XOR) may also be combined. Specifically, the control method for AEC may be one using at least any one of the AND, OR, average, NAND, NOR, and XOR methods.

The mode in which the generation apparatus control unit 403 issues a stop notification is set based on any one of the radiographic apparatus 300, the radiation generation apparatus 324, and the control apparatus 310, for example. The radiographic system 10 may have a mode in which radiation irradiation is not stopped in accordance with a reached radiation dosage. The radiographic system 10 may include a not-illustrated general exposure control sensor (such as an ion chamber and a photo timer) attached outside the radiographic apparatus 300 and stop radiation irradiation in accordance with a radiation dosage. While, in the present exemplary embodiment, the radiographic apparatus 300 includes the generation apparatus control unit 403, the radiographic apparatus 300 may be configured to detect radiation irradiation by using the signal processing unit 224 and perform radiographic imaging without communicating with the radiation generation apparatus 324.

The image control unit 404 stores an image from the reading circuit 222 into the memory 402, and controls communication with the control apparatus 310. The image control unit 404 and the control apparatus 310 exchange radiographic images and control-related information (such as control commands).

The communication switching unit 405 switches the wired communication unit 303 and the wireless communication unit 304 to enable communication by the wired communication unit 303 when the first communication cable 307 is connected to the radiographic apparatus 300, and enable communication by the wireless communication unit 304 when the first communication cable 307 is disconnected from the radiographic apparatus 300.

Figure 6:
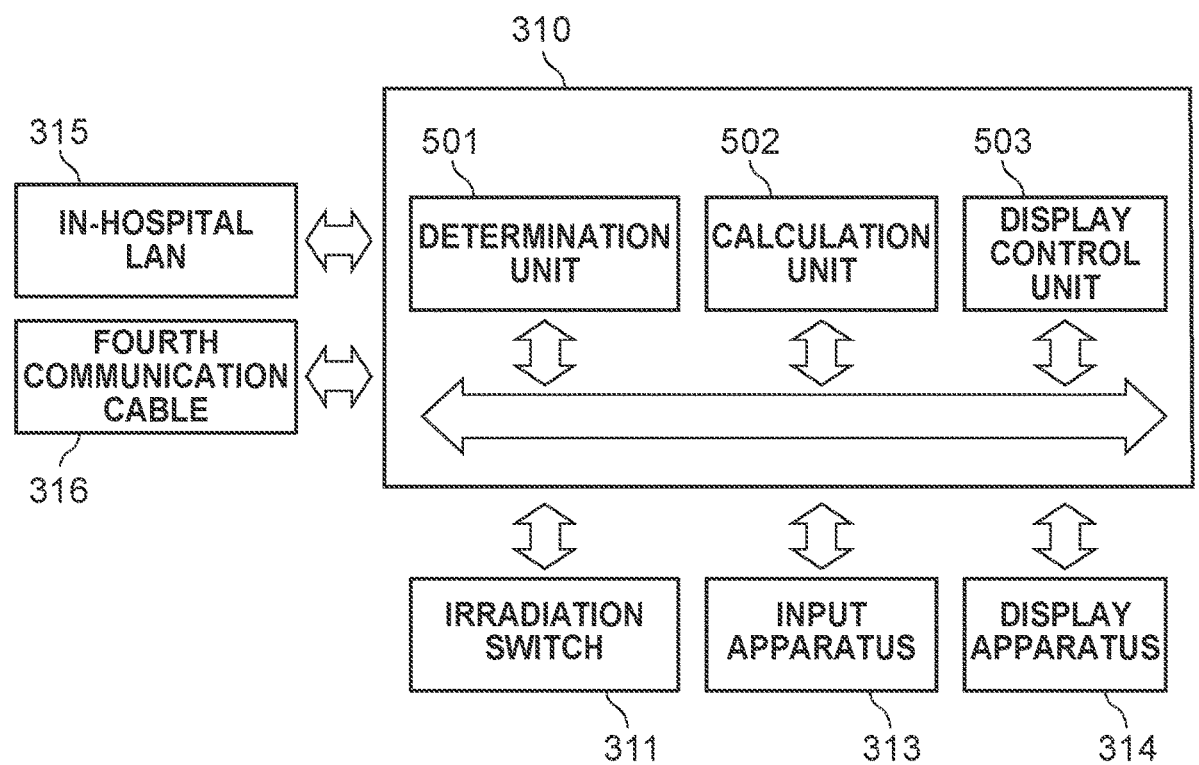
FIG. 6 is a diagram illustrating an example of a control apparatus in the radiographic system.

FIG. 6 is a diagram illustrating the control apparatus 310. As illustrated in FIG. 6, the control apparatus 310 includes a determination unit 501, a calculation unit 502, and a display control unit 503.

The determination unit 501 determines an area (region of interest) to calculate a dose index value in a radiographic image generated by the radiographic apparatus 300. As employed herein, an area to calculate a dose index value is broadly classified into the following two types: a measuring field like the areas A to C in FIG. 3 and the areas K to O in FIG. 4, and a predetermined area like an area P in FIG. 3 and an area Q in FIG. 4. Examples of the latter area is an optional area which includes the entire area of the radiographic image, is specified by the operator 312, or corresponds to an imaging site. Such areas are exemplary and not restrictive.

In the present exemplary embodiment, areas to calculate the dose index value are represented by rectangles as illustrated in FIGS. 8B and 8C, for example. However, this is not restrictive. The areas may be represented by figures of any shape, such as a circular shape and a trapezoidal shape.

Examples of a dose index value to be calculated in an area determined by the determination unit 501 include an EI value. While, in the present exemplary embodiment, an EI value is used as a dose index value, similar techniques can be applied to dose indices in general. A dose index value may be a value proportional or inversely proportional to a pixel value of a radiographic image.

The calculation unit 502 calculates a dose index value of an area determined by the determination unit 501. A dose index target value (for example, target exposure index EIt) which is used to determine that an optimum dose is applied may be set area by area, and the calculation unit 502 may calculate a deviation index (for example, deviation index DI). The target exposure index EIt and the deviation index DI are indices standardized as International Electric Conference (IEC) 62494-1. Specifically, the deviation index DI is calculated by the following equation:

$$DI = 10 \log_{10}(EI/EIt).$$

In general, if a deviation index DI is greater than 0, it is determined that the dose is higher than normal. If the deviation index DI is less than 0, it is determined that the dose is lower than normal.

The dose index target value does not necessarily need to be set area by area. For example, in a case where dose index target values are set for a first area, a second area, and a third area, a first dose index target value may be set for the first and second areas in common, and a second dose index target value may be set for the third area.

The display control unit 503 displays at least one of the indices calculated by the calculation unit 502, namely, the dose index values, dose index target values, and deviation indices, on the display apparatus 314. A method for displaying the at least one of the indices on the display apparatus 314 may be changed in accordance with an imaging condition.

In the present exemplary embodiment, the determination unit 501, the calculation unit 502, and the display control unit 503 are described as functions of the control apparatus 310. However, the radiographic apparatus 300 may be configured to include the functions of the determination unit 501, the calculation unit 502, and the display control unit 503. In other words, at least either the control apparatus 310 or the radiographic apparatus 300 may have functions corresponding to the determination unit 501, the calculation unit 502, and the display control unit 503.

Figure 7:
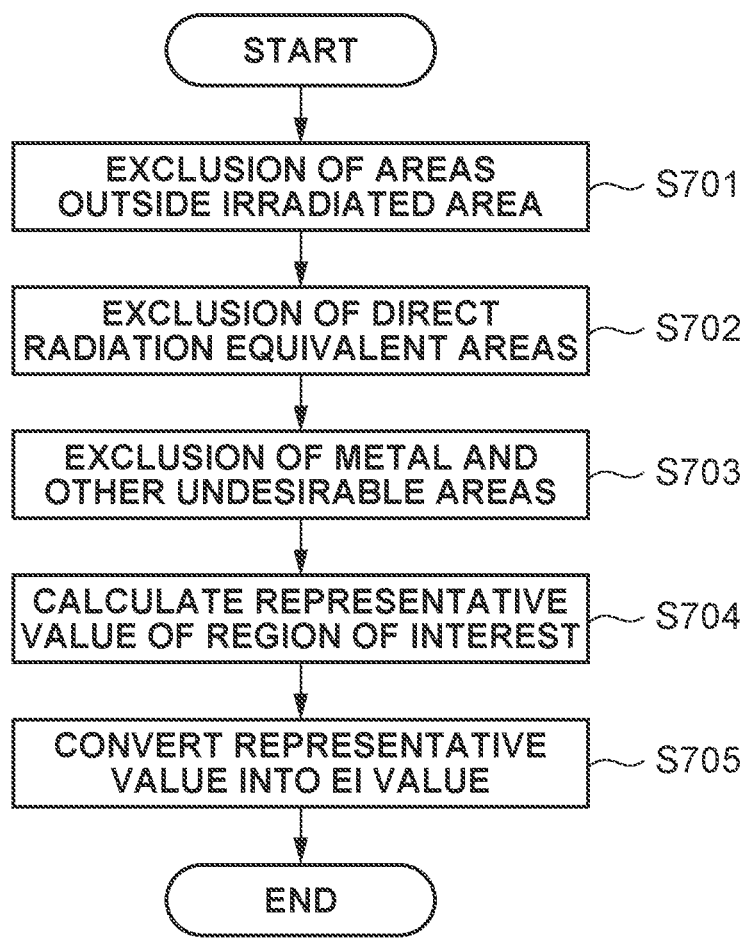
FIG. 7 illustrates an example of a flowchart for calculating an exposure index (EI) value.

A procedure for calculating an EI value from a radiographic image will be described with reference to a flowchart of FIG. 7.

(S701: Exclusion of Areas Outside Irradiated Area)

In step S701, the determination unit 501 initially excludes an area that has not been irradiated with radiation and is outside the region of interest of a diagnostic image, from an EI value calculation area of a radiographic image. Examples of the exclusion method include a method for performing calculations based on collimator information or tube-to-flat panel detector (FPD) distance (FDD) information, a method for extracting an irradiated field from the image using various types of imaging site information determined in advance, and a method for performing determination using machine learning.

(S702: Exclusion of Direct Radiation Equivalent Areas)

In step S702, the determination unit 501 identifies a direct radiation equivalent area and excludes an area outside the region of interest from the EI value calculation area. Examples of the exclusion method include an empirical fixed threshold method, a mode method, a differential histogram method, a percentile method, and discriminant analysis.

(S703: Exclusion of Metal and Other Undesirable Areas)

In step S703, the determination unit 501 excludes, from the EI value calculation area, a low dose area which is in the region of interest but is not to be used as a normal diagnostic image for calculation of a dose index of the region of interest. Examples of the exclusion method include region growing and snakes.

The EI value calculation area is determined by applying the processing so far to the area determined to calculate a dose index value by the determination unit 501 in advance, or by applying the processing to the entire radiographic image and then extracting the area determined to calculate a dose index value by the determination unit 501.

The foregoing processing of steps S701 to S703 may or may not be performed in a selective manner. The processing order is not limited to the foregoing procedure. For example, the exclusion processing of step S703 may be performed before the exclusion processing of step S702.

(S704: Calculate Representative Value of Region of Interest)

In step S704, the calculation unit 502 calculates a representative value of the region of interest in the radiographic image determined by the processing of steps S701 to S703. Examples of a representative value include a pixel value of, for example, an average, a median, and a mode. In a case where there is a plurality of regions of interest like when a plurality of measuring fields is set, a representative value of each of the regions of interest is calculated. The operator 312 can thus identify a dose value in each of the regions of interest.

(S705: Convert Representative Value into EI Value)

In step S705, the calculation unit 502 converts the representative value into a dose, based on a known relationship between an incident dose and a pixel value. The calculation unit 502 then calculates a dose index value by multiplying the converted dose by a constant. More specifically, the calculation unit 502 calculates the dose index value (EI value) by converting the representative value in such a manner that 100=1 µGy. At the same time, the calculation unit 502 calculates a deviation index DI from the dose index target value EIt. The operator 312 checks whether radiographic imaging with an expected radiation dose has been performed.

Next, display examples of dose index values on the display apparatus 314 will be described with reference to FIGS. 8A to 8D and FIGS. 9A to 9C.

The display control unit 503 displays the dose index values calculated by the calculation unit 502 on the display apparatus 314.

Figure 9A:
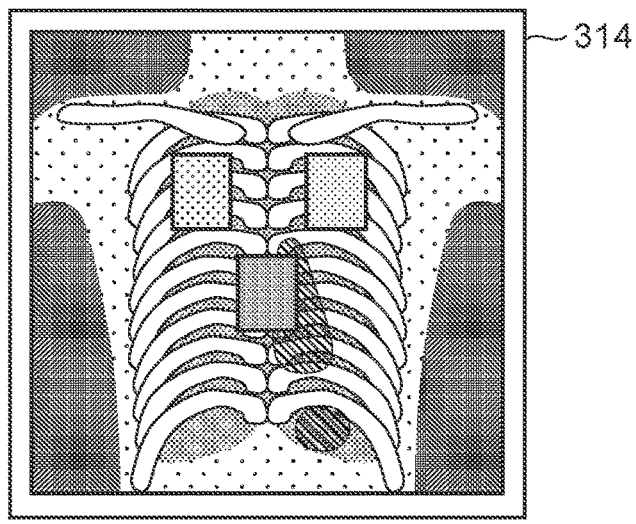
FIGS. 9A to 9C are diagrams each illustrating a display example of the dose index values.
Figure 9B:
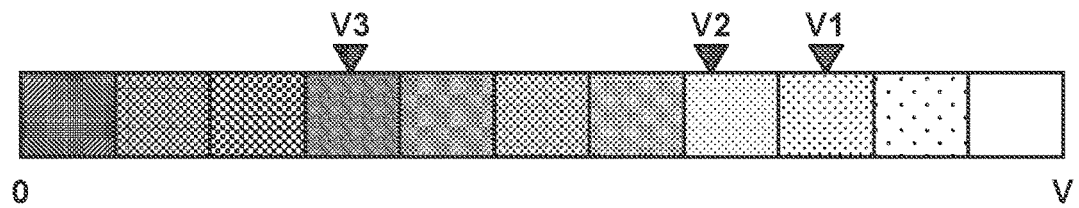
Figure 9C:
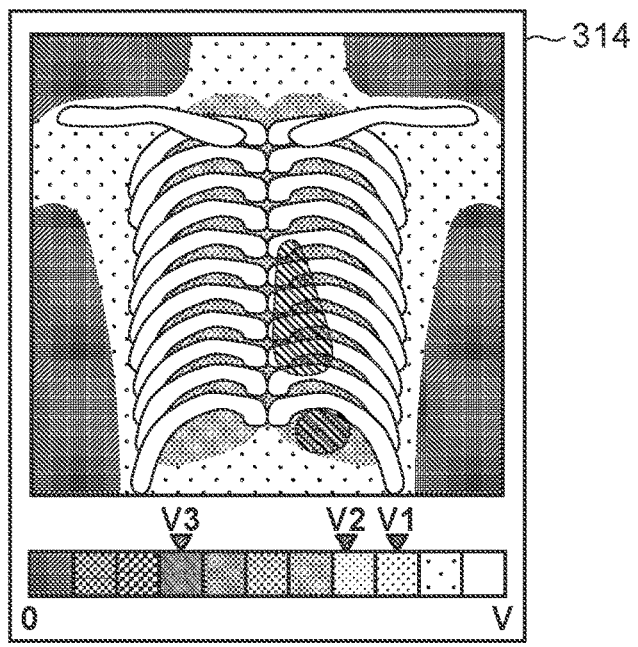

As illustrated in FIG. 8A, the dose index values may be displayed as annotations at corners of a radiographic image. As illustrated in FIG. 8B, each of the dose index values may be superimposed on an image area where the corresponding dose index value has been calculated. Alternatively, the dose index values may be displayed separately from the radiographic image. For example, as illustrated in FIG. 8C, the dose index values may be displayed next to the radiographic image. As illustrated in FIG. 8D, the dose index values may be displayed without the radiographic image. Moreover, as illustrated in FIG. 9A, each of the dose index values may be rendered in a gray scale (or color scale) and displayed on the radiographic image. As illustrated in FIG. 9B, only the gray scale (or color scale) may be separately displayed. As illustrated in FIG. 9C, the radiographic image and the gray scale (or color scale) may be displayed in combination. In other words, at least two or more pieces of information about the values calculated by the calculation unit 502 may be displayed by changing at least either color or tone level.

While FIGS. 8A to 8D and 9A to 9C illustrate examples of displaying the dose index values using text or color, the display method may be defined by any combination of recognizable expressions, such as text, symbols, figures, sizes, color, and shapes. Moreover, the display control unit 503 may display dose index target values and deviation index values along with the dose index values. The dose index target values and the deviation index values may be displayed by the same display method as that of the dose index values or by any other display method. Instead of displaying the dose index values or deviation index values, a warning dialog may be displayed in a case where the dose index values and deviation index reach or exceed a predetermined threshold, for example. Only one such threshold may be set. Thresholds may be set for respective areas where the dose index values are calculated.

In a case where a notification to stop the radiation irradiation is performed, the display control unit 503 may identifiably display, on the display apparatus 314, a measuring field that has been used for determination of stopping the radiation irradiation, among the one or more measuring fields. In a case where the control method is the AND method, one or more measuring fields lastly reached the target dose are identifiably displayed. In a case where the control method is the OR method, the measuring field first reached the threshold is identifiably displayed. In a case where the control method is the average method, all the measuring fields are identifiably displayed. Examples of the method for identifiable display include identifiably displaying text information, and highlighting the measuring field(s) on the radiographic image. The dose index value(s) of the measuring field(s) ultimately used for determination of stopping the radiation irradiation may be displayed. The dose index values of all the measuring fields may be displayed, and the measuring field(s) ultimately used for determination of stopping the radiation irradiation may be marked up.

Next, an operation of the radiographic system 10 during imaging will be described with reference to FIG. 10.

When the radiographic system 10 is powered up and the radiographic apparatus 300 is powered on, the radiographic apparatus 300 performs initialization to enable communication with the control apparatus 310.

(S101: Input Subject Information and Imaging Information)

In step S101, the radiographic system 10 sets subject information, such as an identifier (ID), name, and date of birth of the subject 306, into the control apparatus 310. The radiographic system 10 also sets imaging information, such as an imaging site, a measuring field, and a dose index target value for the subject 306. For example, the subject information and the imaging information may be automatically set by selecting a test order received via the in-hospital LAN 315. The operator 312 may set the imaging information by selecting a predetermined imaging protocol. Yet alternatively, the operator 312 may directly input and set the subject information and the imaging information. The radiographic system 10 sets the measuring field(s) of the radiographic apparatus 300, based on the input information. After the information about the subject 306 and the information about the imaging site are set into the control apparatus 310, the operator 312 fixes the posture of the subject 306 and the radiographic apparatus 300. The operator 312 further inputs a dose, maximum irradiation time, a tube current, a tube voltage, site information, the measuring field(s), and the dose index target value(s) into the control apparatus 310. The control apparatus 310 transmits the input irradiation condition of radiation, site information, measuring field(s), and dose index target value(s) to the radiographic apparatus 300 and the radiation generation apparatus 324. The radiographic system 10 may be configured so that the information is input into the radiation generation apparatus 324 and notified to the control apparatus 310 and the radiographic apparatus 300. Here, the control apparatus 310 may obtain information managed in association with at least either the subject information or the imaging information. For example, information managed in association with the site information may include AEC measuring field selection information, the AEC method for a case where a plurality of measuring fields is selected (such as the AND method), and target cumulative dosage serving as the threshold to stop radiation irradiation. In other words, the control apparatus 310 can obtain information about the AEC control method associated with at least either the subject information or the imaging information. Specifically, for example, in a case where the site information indicates a front chest, the information managed in association with the site information includes selection information for selecting a right measuring field and a left measuring field (areas K and L in FIG. 4) corresponding to both lung fields and the AND method that is an AEC method. In a case where the site information indicates a side chest, the information managed in association with the site information includes selection information for selecting the center measuring field (area M in FIG. 4). In the present exemplary embodiment, the control apparatus 310 is described to obtain the information managed in associated with the input or notified site information in step S101. However, such information may be managed in association with subject information or imaging information different from the site information. For example, the information may be managed in association with an imaging technique, an imaging orientation, an imaging direction, the presence or absence of a grid, or the type of radiographic apparatus.

(S102: Imaging)

After the completion of the imaging preparations, in step S102, the operator 312 presses the irradiation switch 311. In response to the irradiation switch 311 being pressed, the radiation source 325 emits radiation toward the subject 306. Here, the radiographic apparatus 300 communicates with the radiation generation apparatus 324 to control start of radiation irradiation. The radiation irradiating the subject 306 are transmitted through the subject 306 and incident on the radiographic apparatus 300. In a case where the radiographic apparatus 300 is set to use the reached dose monitoring function, the radiographic apparatus 300 detects radiation incident on the measuring field(s) by using the detection pixels 101, and the signal processing unit 224 calculates a cumulative dosage that is a cumulative value of a dose (reached dose) detected in a predetermined period. The imaging apparatus control unit 225 calculates a reference threshold, based on cumulative dosage information from the signal processing unit 224 and the site information and imaging condition input by the operator 312, and determines radiation irradiation stop timing, based on a mode set by the generation apparatus control unit 403. The radiographic apparatus 300 notifies the radiation generation apparatus 324 to stop the radiation irradiation via the first communication cable 307, the communication control apparatus 323, and the third communication cable 327, based on the determined radiation irradiation stop timing. The radiation generation apparatus 324 stops the radiation irradiation based on the notified radiation irradiation stop timing. While the radiographic apparatus 300 issues the notification to stop the radiation irradiation as a result of detection of the radiation, this is not restrictive. The radiographic apparatus 300 may be configured to transmit the reached dose at predetermined time intervals as a result of detection, and the radiation generation apparatus 324 may calculate a cumulative value of the reached dose. After the radiation irradiation is stopped, the radiographic apparatus 300 converts the incident radiation into visible light and then detects the visible light as radiographic image signals by using the photoelectric conversion elements. The radiographic apparatus 300 reads the radiographic image signals by driving the photoelectric conversion elements, and converts the analog signals into digital signals through the AD converter 136 to obtain a radiographic image.

(S103: Receive Radiographic Image)

In step S103, the radiographic system 10 transfers the obtained radiographic image from the radiographic apparatus 300 to the control apparatus 310 via the first communication cable 307, the communication control apparatus 323, and the third communication cable 327. The control apparatus 310 applies image processing to the received digital radiographic image. The control apparatus 310 displays the image-processed radiographic image on the display apparatus 314. The control apparatus 310 thus functions also as an image processing apparatus and a display control apparatus.

(S104: Reached Dose Monitoring Function)

In step S104, the control apparatus 310 determines whether the reached dose monitoring function is enabled. In a case where the reached dose monitoring function is enabled (YES in step S104), the processing proceeds to step S105. On the other hand, in a case where the reached dose monitoring function is not enabled (NO in step S104), the processing proceeds to step S106.

(S105: Determine Measuring field(s) as Calculation Area(s))

In step S105, the determination unit 501 determines the measuring field(s) set in step S101 as a calculation area or areas (EI value calculation area(s)) to calculate radiation dosage. For example, in the case of imaging the lung field, radiographic imaging is often performed on measuring fields set to both lungs. In such a case, the calculation areas to calculate the radiation dosage are the measuring fields set to both lungs. The calculation area(s) determined by the determination unit 501 in step S105 does not necessarily need to be the same as the measuring field(s). For example, a measuring field-based area obtained by the processing illustrated in FIG. 7 may be determined as a calculation area.

(S106: Determine Predetermined Area as Calculation Area)

In step S106, the determination unit 501 determines a predetermined area as a calculation area to calculate radiation dosage. For example, the predetermined area is set by the operator 312 in step S101. In a case where an area that can be determined regardless of the imaging information or the setting by the operator 312, like the entire area of the radiographic image, is set as the predetermined area, the operator 312 does not necessarily need to perform the setting. The radiographic system 10 may be configured so that the calculation area can be changed by the operator 312 after imaging.

While, in the present exemplary embodiment, the calculation area(s) is/are determined based on whether the reached dose monitoring function is enabled, this is not restrictive.

(S107: Calculate Dose Index Value of Each Calculation Area)

In step S107, the control apparatus 310 transmits the received digital radiographic image to the calculation unit 502. The calculation unit 502 calculates the dose index value of each calculation area determined as described above based on the received radiographic image. For example, the calculation unit 502 calculates the dose index value of each of the measuring fields set to both lungs.

(S108: Calculate Deviation Index Value in Each Calculation Area)

In step S108, the calculation unit 502 calculates the deviation index value(s). While, in the present exemplary embodiment, the control apparatus 310 calculates the dose index values and the deviation index values, these values may be calculated by the radiographic apparatus 300 or by another not-illustrated calculation apparatus.

(S109: Display Calculated Values)

In step S109, the control apparatus 310 transfers the dose index values and the deviation index values calculated by the calculation unit 502 to the display control unit 503. The display control unit 503 provides display illustrated in FIGS. 11A to 11C, for example. FIGS. 11A to 11C illustrate an example where the reached dose monitoring function is enabled, the lung field is imaged while measuring fields at both lung areas R1 and R2 illustrated in FIG. 11B are set, and dose index values and deviation index values of the corresponding areas are displayed as illustrated FIGS. 11A and 11C.

Whether to display the calculated values on the display apparatus 314 may be set before imaging or set by the operator 312 after imaging. The display setting may be changed in accordance with the setting of the reached dose monitoring function. Alternatively, a not-illustrated icon or dialog may be controlled to be displayed in a case where the received dose index values and the received deviation index values satisfy a specific condition. Examples of the specific condition include that the dose index values and the deviation index values are greater than predetermined values.

While, in the present exemplary embodiment, an image just captured is taken as an example, images captured in the past may be displayed in a similar manner. The measuring field(s) actually used by the reached dose monitoring function may be obtained from the radiographic apparatus 300 and reflected on the display content. For example, when radiation irradiation is stopped, displaying of which a measuring field or measuring fields are ultimately used for the determination of stopping the radiation irradiation can be performed on the display apparatus 314. In other words, the control apparatus 310 can explicitly display the one or more measuring fields used for the determination of stopping the radiation irradiation based on the control method. In a case where the control method is the AND method, the one or more measuring fields lastly reached the target dose can be explicitly displayed. In a case where the control method is the OR method, the one or more measuring fields first reached the threshold can be explicitly displayed. In a case where the control method is the average method, all the measuring fields can be explicitly displayed. The measuring field(s) may be explicitly displayed using text information. The measuring field(s) may be explicitly displayed at their positions on the radiographic image. The operator 312 can thus easily recognize which one or more of the measuring field(s) has been used for the determination of stopping the radiation irradiation. The operator 312 can also easily recognize which one or more of the measuring field(s) has been used for the determination of stopping the radiation irradiation and the dose index value(s) in the measuring field(s).

In the above-described manner, a series of processes by the radiographic system 10 is performed.

As a result of the foregoing, the operator 312 can appropriately determine whether a desirable amount of radiation is incident on an AEC measuring field during radiographic imaging.

In a case of imaging in which a plurality of regions of interest is set, like when a plurality of measuring fields is set, the operator 312 can determine whether the regions of interest are irradiated with an appropriate amount of radiation by checking the respective dose index values and the deviation index values displayed on the display apparatus 314. For example, in a case where an imaging dose can be reduced by using the reached dose monitoring function and an appropriate amount of radiation is confirmed to be incident on each region of interest, it can be easily determined that the imaging has been appropriately conducted.

In a second exemplary embodiment, a description will be provided of a configuration of a radiographic system 10 that calculates dose index values for a predetermined area and respective AEC measuring fields and displays the dose index values. This enables an operator to appropriately determine whether desirable amounts of radiation are incident on the predetermined area and the respective AEC measuring fields.

Processing by the radiographic system 10 according to the present exemplary embodiment will be described below with reference to FIGS. 12A to 12D to FIG. 14. A functional configuration of the radiographic system 10 is similar to the radiographic system 10 in the first exemplary embodiment, and the redundant description will thus be omitted.

Display examples of dose index values on the display apparatus 314 will initially be described with reference to FIGS. 12A to 12D and 13A to 13C.

Figure 13A:
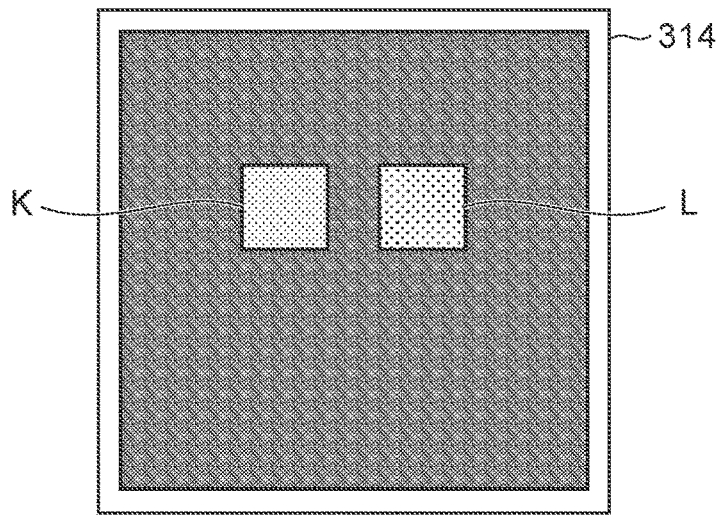
FIGS. 13A to 13C are diagrams each illustrating a display example of the dose index values.
Figure 13B:
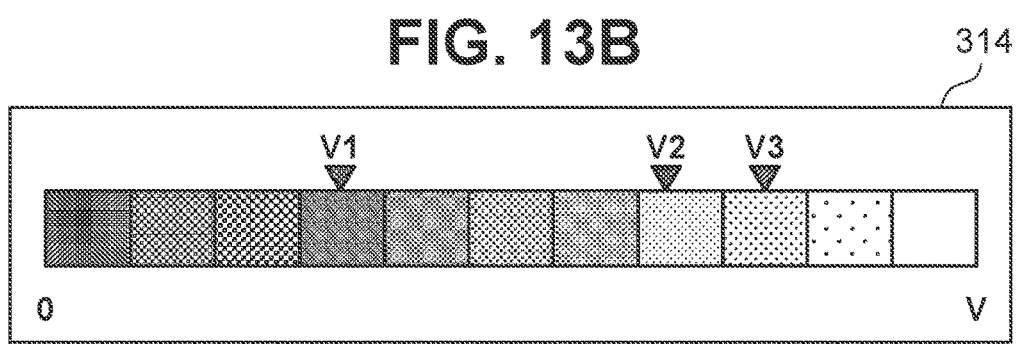
Figure 13C:
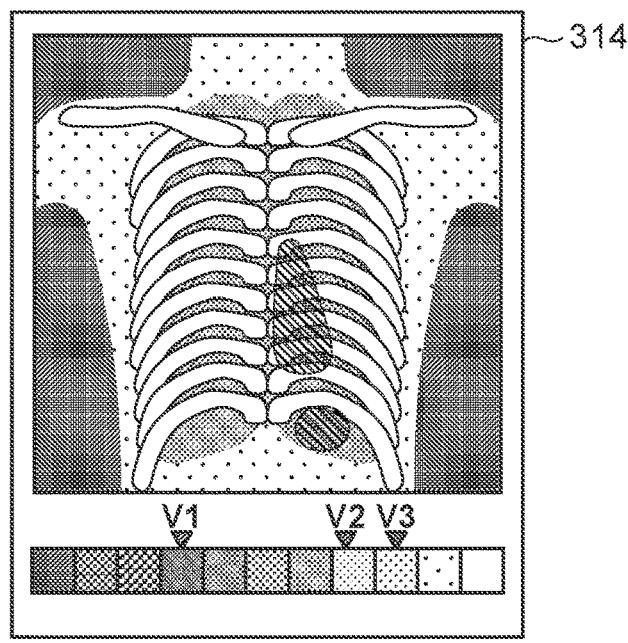

The display control unit 503 displays a first dose index value (in the diagrams, V1) and second dose index values (in the diagrams, V2 and V3) calculated by the calculation unit 502 on the display apparatus 314. As illustrated in FIG. 12A, the first dose index value and the second dose index values may be displayed as annotations at corners of the radiographic image. As illustrated in FIG. 12B, the first dose index value may be displayed at a given position on the radiation image, and the second dose index values may be superimposed at the respective positions of the measuring fields where the respective dose index values are calculated on the radiographic image. As illustrated in FIG. 12C, the dose index values may be displayed separately from the radiographic image. As illustrated in FIG. 12D, the dose index values may be displayed without the radiographic image. Alternatively, as illustrated in FIG. 13A, the dose index values may be rendered in a gray scale (or color scale) and displayed to express relative positions between the radiographic image and the measuring fields on the radiographic image. As illustrated in FIG. 13B, only the gray scale (or color scale) may be separately displayed. As illustrated in FIG. 13C, the radiographic image and the gray scale (or color scale) may be displayed in combination. In other words, at least two or more pieces of information about the values calculated by the calculation unit 502 may be displayed by changing at least either color or tone level.

While FIGS. 12A to 12D and 13A to 13C illustrate examples of displaying the dose index values using text or color, the display method may be defined by any combination of recognizable expressions, such as text, symbols, figures, sizes, color, and shapes. Moreover, the display control unit 503 may also display a first dose index target value, a first deviation index value, second dose index target values, and second deviation index values along with the first dose index value and the second dose index values. The first dose index target value and the first deviation index value may be displayed by a display method similar to or different from that of the first dose index value. The second dose index target values and the second deviation index values may be displayed by a display method similar to or different from that of the second dose index values. Instead of displaying the first dose index target value, the first deviation index value, the second dose index target values, and the second deviation index values, a warning dialog may be displayed in a case where a predetermined threshold is reached or exceeded, for example.

Next, an operation of the radiographic system 10 during imaging according to the second exemplary embodiment will be described with reference to FIG. 14.

(S1401: Input Subject Information and Imaging Information)

In step S1401, the radiographic system 10 sets subject information, such as an identifier (ID), name, and date of birth of the subject 306 into the control apparatus 310. The radiographic system 10 also sets imaging information, such as an imaging site, the measuring field(s), and dose index target value(s) of the subject 306.

For example, the subject information and the imaging information may be automatically set by selecting a test order received via the in-hospital LAN 315. The operator 312 may set the imaging information by selecting a predetermined imaging protocol. Alternatively, the operator 312 may directly input and set the subject information and the imaging information. The radiographic system 10 sets the measuring field(s) of the radiographic apparatus 300 in accordance with the input information. After the information about the subject 306 and the information about the imaging site are set into the control apparatus 310, the operator 312 fixes the posture of the subject 306 and the radiographic apparatus 300. The operator 312 further inputs a dose, maximum irradiation time, a tube current, a tube voltage, site information, the measuring field(s), and the dose index target value(s) into the control apparatus 310. The control apparatus 310 transmits the input irradiation condition of radiation, site information, a measuring field(s), and a dose index target value(s) to the radiographic apparatus 300 and the radiation generation apparatus 324. The radiographic system 10 may be configured so that the information is input into the radiation generation apparatus 324 and notified to the control apparatus 310 and the radiographic apparatus 300.

(S1402: Imaging)

After the completion of the imaging preparations, in step S1402, the operator 312 presses the irradiation switch 311. In response to the irradiation switch 311 being pressed, the radiation source 325 emits radiation toward the subject 306. Here, the radiographic apparatus 300 communicates with the radiation generation apparatus 324 to control start of radiation irradiation. The radiation irradiating the subject 306 are transmitted through the subject 306 and incident on the radiographic apparatus 300. In a case where the radiographic apparatus 300 is set to use the reached dose monitoring function, the radiographic apparatus 300 detects radiation incident on the measuring field(s) by using the detection pixels 101, and the signal processing unit 224 calculates a cumulative dosage that is a cumulative value of a dose (reached dose) detected in a predetermined period. The imaging apparatus control unit 225 calculates a reference threshold based on cumulative dosage information from the signal processing unit 224 and the site information and imaging condition input by the operator 312, and determines radiation irradiation stop timing based on a mode set by the generation apparatus control unit 403. The radiographic apparatus 300 notifies the radiation generation apparatus 324 to stop the radiation irradiation via the first communication cable 307, the communication control apparatus 323, and the third communication cable 327 based on the determined radiation irradiation stop timing. The radiation generation apparatus 324 stops the radiation irradiation based on the notified radiation irradiation stop timing. While the radiographic apparatus 300 issues the notification to stop the radiation irradiation as a result of detection of the radiation, this is not restrictive. The radiographic apparatus 300 may be configured to transmit the reached dose at predetermined time intervals as a result of detection, and the radiation generation apparatus 324 may calculate a cumulative value of the reached dose. After the radiation irradiation is stopped, the radiographic apparatus 300 converts the incident radiation into visible light and then detects the visible light as radiographic image signals by using the photoelectric conversion elements. The radiographic apparatus 300 reads the radiographic image signals by driving the photoelectric conversion elements, and converts the analog signals into digital signals through the AD converter 136 to obtain a radiographic image.

(S1403: Receive Radiographic Image)

In step S1403, the radiographic system 10 transfers the obtained radiographic image from the radiographic apparatus 300 to the control apparatus 310 via the first communication cable 307, the communication control apparatus 323, and the third communication cable 327. The control apparatus 310 applies image processing to the received digital radiographic image. The control apparatus 310 displays the image-processed radiographic image on the display apparatus 314. The control apparatus 310 thus functions also as an image processing apparatus and a display control apparatus.
(S1404: Calculate Dose Index Values in Regions of Interest)

In step S1404, the control apparatus 310 transfers the received digital radiographic image data (digital radiographic image) to the calculation unit 502. The calculation unit 502 calculates dose index values of a plurality of regions of interest, based on the received radiographic image data. More specifically, the calculation unit 502 calculates a first dose index value from a predetermined area of the radiographic image generated based on the received radiation image data. In the following description, the predetermined area refers to the entire radiographic image. However, this is not restrictive. The calculation unit 502 also calculates a second dose index value or values based on the measuring field(s) in the radiographic image generated based on the received radiographic image data.
(S1405: Calculate Deviation Index Values in Regions of Interest)

In step S1405, the calculation unit 502 calculates deviation index values. While in the present exemplary embodiment the control apparatus 310 calculates the dose index values and the deviation index values, the dose index values and deviation index values may be calculated by the radiographic apparatus 300 or by another not-illustrated calculation apparatus.
(S1406: Display Calculated Values)

In step S1406, the calculation unit 502 transfers the first dose index value, the second dose index value(s), the first dose index target value, the second dose index target value(s), the first deviation index value, and the second deviation index value(s) to the display control unit 503. The display control unit 503 provides display such as illustrated in FIGS. 12A to 12D. In other words, the display control unit 503 displays information about the values calculated by the calculation unit 502 on the display apparatus 314.

FIGS. 12A to 12D illustrate examples of a case where the reached dose monitoring function is enabled, both lung areas K and L illustrated in FIG. 12B are set as measuring fields, and the lung field is imaged. Dose index values (first dose index value and second dose index values) and deviation index values (first deviation index value and second deviation index values) of the entire radiographic image and the areas of the respective measuring fields to be monitored are displayed as illustrated in FIGS. 12A to 12C.

Displaying the dose index values (first dose index value and second dose index values) and the deviation index values (first deviation index value and second deviation index values) of the entire radiographic image and the areas of the respective measuring fields to be monitored enables the operator 312 to check whether the doses to the region of interest of the radiographic image and the measuring fields set to be monitored are appropriate. Whether to display the calculated values on the display apparatus 314 may be set before imaging or set by the operator 312 after imaging. The display setting may be changed in accordance with the setting of the reached dose monitoring function. Alternatively, a not-illustrate icon or dialog may be controlled to be displayed in a case where the first dose index value and the second dose index value and the first deviation index value and the second deviation index value satisfy a specific condition. Examples of the specific condition include that any one of the first dose index value and the second dose index value and the first deviation index value and the second deviation index value is greater than a predetermined value.

While, in the present exemplary embodiment, an image just captured is taken as an example, images captured in the past may be displayed in a similar manner. To calculate the second dose index value(s), the calculation unit 502 may obtain the measuring field(s) used by the reached dose monitoring function from the radiographic apparatus 300 or the image control unit 404, and reflect the measuring field(s) on the display content.

In such a manner, a series of processes by the radiographic system 10 according to the second exemplary embodiment is performed.

As a result of the foregoing, the operator 312 can appropriately determine whether desirable amounts of radiation are incident on the predetermined area and the respective AEC measuring fields by checking the first dose index value and the second dose index value displayed on the display apparatus 314. For example, in a case where the predetermined area is the entire area of the radiographic image, the operator 312 can check both the dose index value of the radiation irradiating the entire area and the dose index values of the radiation irradiating the measuring fields in a subsequent step.

For example, in a case where an imaging dose can be reduced by using the reached dose monitoring function and appropriate amounts of radiation are confirmed to be incident on the region of interest of the radiographic image and the respective measuring fields, the operator 312 can easily determine that the imaging has been appropriately conducted.

Other Exemplary Embodiments

An exemplary embodiment of the present invention can also be implemented by processing for supplying a program for implementing one or more functions of the foregoing exemplary embodiments to a system or an apparatus via a network or a storage medium, and reading and executing the program by one or more processors in a computer of the system or apparatus. Circuits for implementing one or more of the functions may be used for implementation.

The processors and circuits may include a CPU, a micro processing unit (MPU), a graphics processing unit (GPU), an application-specific integrated circuit (ASIC), and a field-programmable gate array (FPGA). The processors and circuits may also include a digital signal processor (DSP), a data flow processor (DFP), and a neural processing unit (NPU).

The radiographic system according to each of the foregoing exemplary embodiments may be implemented as a single apparatus. A plurality of apparatuses may be communicably combined to execute the foregoing processing. Both cases are covered by the exemplary embodiments of the present invention. A common server apparatus or a group of servers may be configured to execute the foregoing processing. A plurality of apparatuses constituting the radiographic system may be capable of communication at a predetermined communication rate, and does not need to be located in the same facility or in the same country.

An exemplary embodiment of the present invention may cover a mode in which a software program for implementing the functions of the foregoing exemplary embodiments is supplied to a system or an apparatus, and a computer of the system or apparatus reads and executes the supplied program code.

The program code installed on the computer to implement the processing of the exemplary embodiment by the computer is therefore also an exemplary embodiment of the present invention. An operating system (OS) running on the computer may perform part or all of the actual processing based on instructions included in the program read by the computer, in which case the functions of the foregoing exemplary embodiments are implemented by the processing.

The present invention is not limited to the foregoing exemplary embodiments. Various modifications (including organic combinations of the exemplary embodiments) can be made, and such modifications are not excluded from the scope of the present invention. Examples of the modifications may include making the exemplary embodiments adaptable to capturing of moving images as well as still images.

In other words, all configurations obtained by combining the foregoing exemplary embodiments are also intended to be covered by the exemplary embodiments of the present invention.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Applications No. 2021-059044, filed Mar. 31, 2021, No. 2021-059045, filed Mar. 31, 2021, and No. 2021-059046, filed Mar. 31, 2021, which are hereby incorporated by reference herein in their entirety.

What is claimed is:

1. A radiographic system that includes a radiation generation apparatus configured to emit radiation, a radiographic apparatus configured to generate a radiographic image based on the radiation, a control apparatus configured to communicate with the radiographic apparatus to receive the radiographic image and control operation, the radiographic system comprising:
   an obtaining unit configured to obtain a plurality of dose index values using the radiation image generated based on the radiation; and
   a setting unit configured to set a dose index target value corresponding to the plurality of dose index values,
   wherein the obtaining unit is configured to obtain a plurality of deviation index values using the plurality of dose index values and the dose index target value.

2. The radiographic system according to claim 1, wherein the obtaining unit is configured to obtain the plurality of dose index values each of which corresponds to different one of a plurality of regions of interest.

3. The radiographic system according to claim 2, wherein the obtaining unit is configured to further obtain a dose index value of a predetermined area in the radiographic image.

4. The radiographic system according to claim 1, further comprising:
   a dose detection unit configured to detect a dose reached the dose detection unit during radiation irradiation; and
   a notification unit configured to issue, in a case where the reached dose is more than or equal to a predetermined threshold, a notification to stop the radiation irradiation from the radiation generation apparatus,
   wherein the obtaining unit is configured to obtain the plurality of dose index values of at least two or more areas in the radiographic image, the at least two or more areas being based on the dose detection unit.

5. The radiographic system according to claim 4, wherein the notification unit is configured to issue the notification to stop the radiation irradiation from the radiographic generation apparatus, based on an automatic exposure control method associated with at least either subject information or imaging information.

6. The radiographic system according to claim 4, wherein the notification unit is configured to issue, in a case where a dose reached any one of a plurality of the dose detection units is more than or equal to the predetermined threshold, the notification to stop the radiation irradiation from the radiation generation apparatus.

7. The radiographic system according to claim 4, wherein the notification unit is configured to issue, in a case where an average of doses reached a plurality of the dose detection units is more than or equal to the predetermined threshold, the notification to stop the radiation irradiation from the radiation generation apparatus.

8. The radiographic system according to claim 4, wherein the notification unit is configured to issue, in a case where all doses reached a plurality of the dose detection units are more than or equal to the predetermined threshold, the notification to stop the radiation irradiation by the radiation generation apparatus.

9. The radiographic system according to claim 1, wherein the dose index value is a value proportional to a pixel value of the radiographic image.

10. The radiographic system according to claim 1, wherein the dose index value is a value inversely proportional to a pixel value of the radiographic image.

11. The radiographic system according to claim 1, further comprising:
a display control unit configured to display information about a value obtained by the obtaining unit on a display unit,
wherein the display control unit is configured to display the information about the value obtained by the obtaining unit on the display unit by one of the following ways:
(a) displaying the information using at least one recognizable expression among text, color, a symbol, a figure, a size, and a shape;
(b) superimposing the information on the radiographic image; and
(c) displaying the information in an area different from the radiographic image.

12. A control apparatus comprising:
a communication unit configured to communicate with a radiographic apparatus;
a receiving unit configured to receive a radiographic image from the radiographic apparatus;
an obtaining unit configured to obtain information, about an automatic exposure control method, associated with at least either subject information or imaging information including a detected dose amount reached during radiation irradiation; and
a notification unit configured to issue, in a case where the reached dose is more than or equal to a predetermined threshold, a notification to stop the radiation irradiation from a radiation generation apparatus,
wherein the reached dose corresponds to a region of interest representing an area that is less than a measuring field associated with the radiographic image.

13. A radiographic method of a radiographic system including a radiation generation apparatus configured to emit radiation, a radiographic apparatus configured to generate a radiographic image based on the radiation, and a control apparatus configured to communicate with the radiographic apparatus to receive the radiographic image and control operation, the radiographic method comprising:
obtaining a plurality of dose index values using the radiographic image based on the radiation;
setting a dose index target value corresponding to the plurality of dose index values; and
obtaining a plurality of deviation index values using the plurality of dose index values and the dose index target value.

14. The radiographic method according to claim 13, further comprising:
detecting, by a dose detection unit, a dose reached the dose detection unit during radiation irradiation; and
issuing, in a case where the reached dose is more than or equal to a predetermined threshold, a notification to stop the radiation irradiation from the radiation generation apparatus,
wherein in the obtaining, the plurality of dose index values of at least two or more areas in the radiographic image is obtained, the at least two or more areas being based on the dose detection unit.

15. A non-transitory computer-readable storage medium storing a program for causing a computer to execute the radiographic method according to claim 13.

16. A radiographic system that includes a radiation generation apparatus configured to emit radiation, a radiographic apparatus configured to generate a radiographic image based on the radiation, a control apparatus configured to communicate with the radiographic apparatus to receive the radiographic image and control operation, the radiographic system comprising:
an obtaining unit configured to obtain a plurality of dose index values using the radiation image generated based on the radiation;
a dose detection unit configured to detect a dose reached during radiation irradiation; and
a notification unit configured to issue, in a case where the reached dose is more than or equal to a predetermined threshold, a notification to stop the radiation irradiation from the radiation generation apparatus,
wherein the reached dose corresponds to a region of interest representing an area that is less than a measuring field associated with the radiographic image.

* * * * *